United States Patent
Sriwongjanya et al.

(10) Patent No.: US 6,994,871 B2
(45) Date of Patent: Feb. 7, 2006

(54) ONCE A DAY ANTIHISTAMINE AND DECONGESTANT FORMULATION

(75) Inventors: Mongkol Sriwongjanya, Davie, FL (US); Timothy Weng, Bayside, NY (US); David Barman, North Miami Beach, FL (US); Unchalee Kositprapa, Davie, FL (US)

(73) Assignee: Andrx Pharmaceuticals, Inc., Davie, FL (US)

(*) Notice: Subject to any disclaimer, the term of this patent is extended or adjusted under 35 U.S.C. 154(b) by 461 days.

(21) Appl. No.: 10/244,452

(22) Filed: Sep. 16, 2002

(65) Prior Publication Data
US 2003/0049319 A1    Mar. 13, 2003

Related U.S. Application Data

(63) Continuation-in-part of application No. 09/706,624, filed on Nov. 6, 2000, now abandoned.

(51) Int. Cl.
  *A61K 9/20* (2006.01)
  *A61K 9/22* (2006.01)
  *A61K 9/24* (2006.01)
  *A61K 9/26* (2006.01)

(52) U.S. Cl. .................. 424/464; 424/468; 424/469; 424/470; 424/471; 424/472; 424/473

(58) Field of Classification Search ............... 424/464, 424/468, 469, 470, 471, 472, 473
See application file for complete search history.

(56) References Cited

U.S. PATENT DOCUMENTS

| | | |
|---|---|---|
| 4,181,719 A | 1/1980 | Margetts et al. |
| 4,282,233 A | 8/1981 | Vilani |
| 4,369,172 A | 1/1983 | Schor et al. |
| 4,552,899 A | 11/1985 | Sunshine et al. |
| 4,576,645 A | 3/1986 | Ravel et al. |
| 4,632,821 A | 12/1986 | Peters et al. |
| 4,650,807 A | 3/1987 | Findlay et al. |
| 4,659,716 A | 4/1987 | Villani et al. |
| 4,692,462 A | 9/1987 | Banerjee |
| 4,695,591 A | 9/1987 | Hanna et al. |
| 4,749,711 A | 6/1988 | Sunshine et al. |
| 4,749,721 A | 6/1988 | Sunshine et al. |
| 4,749,722 A | 6/1988 | Sunshine et al. |
| 4,758,424 A | 7/1988 | Denick, Jr. et al. |
| 4,762,709 A | 8/1988 | Sheumaker |
| 4,772,475 A * | 9/1988 | Fukui et al. ............... 424/468 |
| 4,777,170 A | 10/1988 | Heinrich |
| 4,792,452 A | 12/1988 | Howard et al. |
| 4,800,087 A | 1/1989 | Mehta |
| 4,801,461 A | 1/1989 | Hamel et al. |
| 4,834,985 A | 5/1989 | Elger et al. |
| 4,839,354 A | 6/1989 | Sunshine et al. |
| 4,915,952 A | 4/1990 | Ayer et al. |

(Continued)

OTHER PUBLICATIONS

Using METHOCEL Cellulose Ethers for Controlled Release of Drugs in Hydrophilic Matrix Systems. Jul. 2000 The Dow Chemical Company.

*Primary Examiner*—Thurman K. Page
*Assistant Examiner*—S. Tran
(74) *Attorney, Agent, or Firm*—Hedman & Costigan, P.C.

(57) ABSTRACT

A controlled release pharmaceutical formulation for the administration of an antihistamine and decongestant to a patient wherein the formulation employs a compressed matrix core for the controlled release of a decongestant and an immediate release coating for the immediate release of the antihistamine.

26 Claims, 5 Drawing Sheets

U.S. PATENT DOCUMENTS

| | | | |
|---|---|---|---|
| 4,915,953 A | 4/1990 | Jordan et al. | |
| 4,952,402 A | 8/1990 | Sparks et al. | |
| 4,959,219 A | 9/1990 | Chow et al. | |
| 4,990,535 A | 2/1991 | Cho et al. | |
| 4,996,047 A | 2/1991 | Kelleher et al. | |
| 4,996,061 A | 2/1991 | Webb et al. | |
| 4,999,189 A | 3/1991 | Kogan et al. | |
| 4,999,226 A | 3/1991 | Schock et al. | |
| 5,004,613 A | 4/1991 | Radebaugh et al. | |
| 5,023,076 A | 6/1991 | Ayer et al. | |
| 5,024,997 A | 6/1991 | Motola et al. | |
| 5,025,019 A | 6/1991 | Sunshine et al. | |
| 5,073,380 A | 12/1991 | Babu et al. | |
| 5,084,278 A | 1/1992 | Mehta | |
| 5,100,675 A | 3/1992 | Cho et al. | |
| 5,126,145 A | 6/1992 | Evenstad et al. | |
| 5,141,961 A | 8/1992 | Coapman | |
| 5,169,638 A | 12/1992 | Dennis et al. | |
| 5,215,755 A | 6/1993 | Roche et al. | |
| 5,272,137 A | 12/1993 | Blasé et al. | |
| 5,288,503 A | 2/1994 | Wood et al. | |
| 5,296,233 A | 3/1994 | Batista et al. | |
| 5,314,697 A * | 5/1994 | Kwan et al. | 424/480 |
| 5,385,941 A | 1/1995 | Fawzi et al. | |
| 5,405,617 A | 4/1995 | Gowan, Jr. et al. | |
| 5,409,907 A | 4/1995 | Blasé et al. | |
| 5,429,825 A | 7/1995 | Reo et al. | |
| 5,431,916 A | 7/1995 | White | |
| 5,451,409 A | 9/1995 | Rencher et al. | |
| 5,458,879 A | 10/1995 | Singh et al. | |
| 5,466,865 A | 11/1995 | Geyer et al. | |
| 5,489,436 A | 2/1996 | Hoy et al. | |
| 5,510,389 A | 4/1996 | Dhabhar | |
| 5,518,730 A | 5/1996 | Fuisz | |
| 5,529,783 A | 6/1996 | Burke et al. | |
| 5,543,405 A | 8/1996 | Keown et al. | |
| 5,560,913 A | 10/1996 | Kupper | |
| 5,560,921 A | 10/1996 | Damani et al. | |
| 5,595,997 A | 1/1997 | Aberg et al. | |
| 5,602,182 A | 2/1997 | Popli et al. | |
| 5,616,621 A | 4/1997 | Popli et al. | |
| 5,641,512 A | 6/1997 | Cimiluca | |
| 5,648,358 A | 7/1997 | Mitra | |
| 5,654,005 A | 8/1997 | Chen et al. | |
| 5,658,589 A | 8/1997 | Parekh et al. | |
| 5,658,919 A | 8/1997 | Ratnaraj et al. | |
| 5,660,833 A | 8/1997 | Medenica | |
| 5,662,936 A * | 9/1997 | de Haan et al. | 424/479 |
| 5,663,415 A | 9/1997 | Chopdekar et al. | |
| 5,681,577 A | 10/1997 | Lech et al. | |
| 5,691,370 A | 11/1997 | Cupps et al. | |
| 5,698,220 A | 12/1997 | Cardinal et al. | |
| 5,759,579 A | 6/1998 | Singh et al. | |
| 5,763,449 A | 6/1998 | Anaebonam et al. | |
| 5,795,574 A | 8/1998 | Breton et al. | |
| 5,807,579 A * | 9/1998 | Vilkov et al. | 424/469 |
| 5,827,852 A | 10/1998 | Russell et al. | |
| 5,834,019 A | 11/1998 | Gergely et al. | |
| 5,837,379 A | 11/1998 | Chen et al. | |
| 5,840,337 A | 11/1998 | Cody et al. | |
| 5,858,409 A | 1/1999 | Karetny et al. | |
| 5,859,060 A | 1/1999 | Platt | |
| 5,869,098 A | 2/1999 | Misra et al. | |
| 5,869,479 A | 2/1999 | Kreutner et al. | |
| 5,876,752 A | 3/1999 | Herbig et al. | |
| 5,876,759 A | 3/1999 | Gowan, Jr. | |
| 5,881,926 A | 3/1999 | Ross | |
| 5,891,476 A | 4/1999 | Reo et al. | |
| 5,895,663 A | 4/1999 | Irwin et al. | |
| 5,916,590 A | 6/1999 | Cody et al. | |
| 5,919,481 A | 7/1999 | Cody et al. | |
| 5,922,352 A | 7/1999 | Chen et al. | |
| 6,039,974 A * | 3/2000 | MacLaren et al. | 424/472 |

* cited by examiner

ONCE A DAY ANTIHISTAMINE AND DECONGESTANT FORMULATION

This is a continuation in part of application Ser. No. 09/706,624, filed Nov. 6, 2000, now abandoned.

FIELD OF THE INVENTION

The present invention relates to field of oral dosage forms.

BACKGROUND OF THE INVENTION

The present invention relates to a once daily unit dosage form comprising a combination of an antihistamine and a decongestant. The unit dosage form is useful in treating patients with colds, flu and other upper respiratory diseases.

Antihistamines include piperidinoalkanol derivatives which are disclosed in U.S. Pat. No. 4,996,061 and incorporated herein by reference. Piperidinoalkanol compounds are useful as antihistamines, antiallergy agents, and bronchodialators. Loratadine is a specific type of piperidinoalkanol and is disclosed in U.S. Pat. No. 4,282,233 as an antihistamine with little or no sedative effect.

Antihistamines are often administered in combination with sympathomimetic or decongestant drugs. Sympathomimetic drugs such as pseudoephedrine, phenylephrine and phenylpropanolamine are recognized by those skilled in the art as therapeutic agents effective for the relief of nasal congestion.

One common combination of antihistamine and sympathomimetic or decongestant is loratadine and pseudoephedrine. See for example U.S. Pat. No. 5,100,675 which is incorporated herein by reference. Loratadine and pseudoephedrine are sold commercially by Schering under the trade name CLARITIN® D24.

Once a day formulations containing a combination of loratadine and pseudoephedrine have been described. These once a day formulations have been undesirable for many reasons including deficiencies in safety, effectiveness and ease of manufacture. In order for a once a day formulation containing loratadine and pseudoephedrine to be effective it must provide a pseudoephedrine dissolution profile for periods longer than 12 hours without interfering with the safety and effectiveness of loratadine. A once a day formulation of loratadine and pseudoephedrine is described in U.S. Pat. No. 5,314,697. This formulation uses three specific polymers in the tablet core wherein the polymers must be present in specific amounts. This formulation further employs a wet granulate that must be dried. The use of multiple polymers in specified amounts and a wet granulate makes the manufacturing process of the tablets complex and time consuming.

It is an objective of the present invention to provide a safe and effective once a day dosage formulation containing both an antihistamine and a decongestant in which a tablet core can be directly compressed and is therefore easy to manufacture.

It is a further object of this present invention to provide a safe and effective once a day antihistamine and decongestant formulation which does not require a complex mixture of wetted polymers in the delayed release or matrix core of the formulation.

SUMMARY OF THE INVENTION

The present invention is a controlled release pharmaceutical formulation comprising effective amounts of both an antihistamine and a decongestant that is easy to manufacture. A preferred embodiment of the present invention comprises:

(A) a compressed matrix core which comprises:
    (i) a decongestant or pharmaceutically acceptable salt thereof;
    (ii) a hydrogel forming polymer;
    (iii) optionally, a filler;
    (iv) optionally, a glidant;
    (v) optionally, one or more lubricants;
(b) an immediate release coating on said compressed matrix core which comprises an antihistamine, preferably a non-sedating antihistamine, and a binder or film forming material which allows for immediate release of the antihistamine, and
(c) optionally, a coloring agent.
(d) optionally, a polishing agent covering said immediate release coating These and other objects of the invention will become apparent from a review of this specification.

DETAILED DESCRIPTION OF THE INVENTION

I. Compressed Matrix Core

Figure 1:
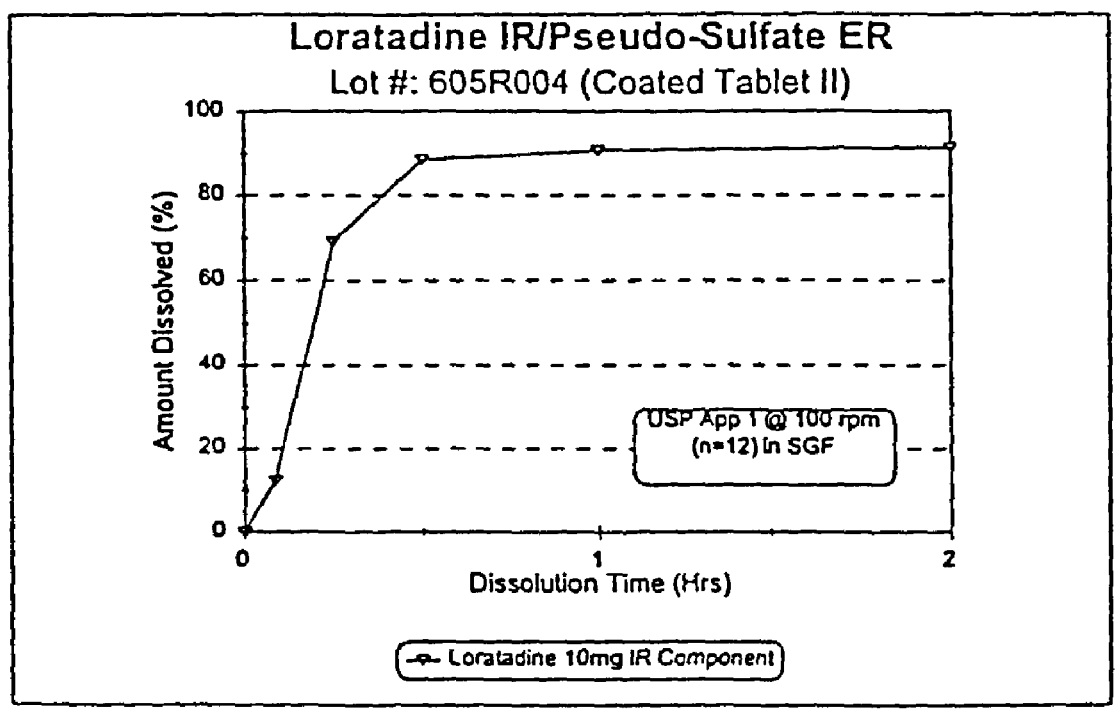
FIG. 1 is a graph which shows the in vitro dissolution rate of an antihistamine from a tablet of a preferred embodiment of the present invention in simulated gastric fluid (SGF) buffer.

The core tablet formulation of the invention is prepared by blending the following materials:

TABLE I

| Matrix Core | Preferred | More Preferred |
| --- | --- | --- |
| Decongestant | 10–50% | 20–40% |
| Hydrogel Forming polymer | 50–90% | 55–75% |
| Filler | 0–20% | 5–15% |
| Antiadherent | 0–5% | 0.01–2% |
| Lubricant(s) | 0–10% | 0.01–5% |

The above percentages are based on the total weight of the matrix core. Once the ingredients are blended they can be pressed or extruded into a core using conventional tabletting techniques as described in Remington's Pharmaceutical Sciences 18$^{th}$ Ed. which is incorporated by reference.

The preferred decongestant is pseudoephedrine. Other possible decongestants include but are not limited to phenylepherine and phenylpropanolamine and other sympathomimetic drugs as well as pharmacologically acceptable salts thereof. The term "pharmacologically acceptable salts" encompasses both organic and inorganic salts including, for example sodium, hydrochloric, hydrofluoric, sulfuric, sulfonic, tartic, fumaric, hydrobromic, glycolic, citric, maleic, sulfate, phosphoric, succinic, acetic, nitric, benzoic, ascorbic, p-toluene sulfonic, benzenesulfonic, naphthalenesulfonic, propionic, and the like.

The hydrogel forming polymer is preferably a single pharmaceutically acceptable polymeric substance such as hydroxypropyl methylcellulose. The hydroxypropyl methylcellulose of the present invention is the U.S.P. substitution type 2208 and should have an average molecular weight above 100,000, preferably above 200,000. The methoxy content of the hydroxypropyl methycellulose should be approximately 19–24 weight percent and the hydroxypropyl methylcellulose should be approximately 7.5 to 8.5 weight percent. A suitable grade of hydroxypropyl is available from Dow Chemical Co. of Midland, Mich. under the trade name METHOCEL K100M which exhibits a viscosity in a 2% aqueous solution of approximately 100,000 cps. An embodiment of the present invention employs a hydroxypropyl methylcellulose with an average molecular weight of 180,000 to 220,000.

Other hydrogel forming polymers that can be used include carboxymethylcellulose calcium, carboxymethylcellulose sodium, guar gum, hydroxyethyl cellulose, hydroxypropyl cellulose, methyl cellulose, acrylic acid crosslinked with polyalkenyl ethers or divinyl glycol, sodium alginate and poly(ethylene oxide) (POLYOX™).

The preferred filler is lactose monohydrate (spray dried). Other fillers such as starch, dextrose, sucrose, hydroxypropyl cellulose, microcrystalline cellulose and the like may be added.

A fumed colloidal silicon dioxide such as Cab-O-Sil®, M5 may be used as the glidant.

A tablet lubricant may be added to the compressed core matrix. Examples of suitable tablet lubricants include magnesium stearate or glyceryl mono-stearate. Eastman® 600P is a commercially available material that may also be used as a lubricant. In a preferred embodiment the lubricants are passed separately through a mesh screen and then blended with a mixture of decongestant, hydrogel forming polymer, filler and glidant which has been passed through a Comil.

It was found that cores compressed using a pre-compression force yielded better tablets. The precompression force should be between 1 to 7 kp preferably 2 to 5 kp. When observed under the microscope, tablets without pre-compression force showed signs of premature capping around the edge area while these defects on tablet edges were not found on tablets compressed using pre-compression force. Surprisingly, tablets without pre-compression had good friability. When subsequently coated, tablets manufactured using a pre-compression force displayed negligible defective edges. In order to prevent the compressed tablet cores from sticking to the tooling, the hardness of the cores should be greater than 18 kp, preferably 20–24 kp.

II. Immediate Release Coating Coated Tablet

The immediate release coating containing an antihistamine, preferably a non-sedating antihistamine is coated directly onto the matrix core or applied over a sealed coated matrix core. The immediate release coating comprises a non-sedating antihistamine and a film forming material or binder and optionally other conventional additives such as lubricants, fillers and antiadherents.

The immediate release coating may be applied by any conventional technique such as pan coating or spray coating. In the preferred embodiment the immediate release coating is applied by spraying an aqueous solution or suspension over a pan containing the matrix core tablets. After the immediate release coating is applied to the matrix core the once a day matrix tablet will comprise:

| Drug Layering | Preferred | More Preferred |
| --- | --- | --- |
| Compressed matrix core | 40–100% | 75–95% |
| Non-Sedating Antihistamine | 0.01–10% | 0.1–5% |
| Binder | 0–20% | 0.5–10% |
| Glidant | 0–10% | 0.1–5% |
| Lubricant | 0–10% | 0.1–5% |

The above percentages are based upon the total weight of the once daily drug formulation or matrix tablet.

The film forming material or binder employ in the immediate release coating preferably comprises Opadry Clear®, YS-1-7006 which contains 91 wt % hydroxypropyl methylcellulose (E-6), 9 wt % polyethylene glycol and is applied in a 8–15% w/w solution in purified water. An antiadherent material such as sodium lauryl sulfate may be used as well. A lubricant such as talc can optionally be used.

III. Polishing Agent

A polishing agent such as candellila wax may optionally be applied to the immediate release coating by any of the conventional coating techniques described in Remington's Pharmaceutical Sciences 18$^{th}$ Ed which is incorporated by reference. The once a day formulation prepared in accordance with the present invention will preferably exhibit the following antihistamine release rate in 900 ml of SGF buffer, pH 1.2 using a USP Apparatus I at 100 rpm, at 37° C.

| Time | Amount dissolved (Preferred) | Amount Dissolved (Most preferred) |
| --- | --- | --- |
| 0.25 Hours | 40–80% | NLT 50% |
| 0.50 Hours | 65%–95% % | NLT 75% |
| 1.0 Hours | NLT-85% | NLT 90% |

* NLT = not less than.

The once a day formulation prepared in accordance with the present invention will preferably exhibit the following decongestant release rate in 900 ml of SGF buffer, pH 1.2 using a USP Apparatus I at 100 rpm, 37° C.

| Time | Amount dissolved (Preferred) | Amount Dissolved (Most preferred) |
| --- | --- | --- |
| 1.0 Hours | 0–50% | 10–40% |
| 2.0 Hours | 10–60% % | 15–45% |
| 4.0 Hours | 20–70% | 25–60% |
| 8.0 Hours | 30–85% | 35–80% |
| 12.0 Hours | NLT 45% | NLT 50% |
| 20.0 Hours | NLT 60% | NLT 70% |

*NLT = not less than

DESCRIPTION OF THE PREFERRED EMBODIMENT

An antihistamine/decongestant tablet containing loratadine as an antihistamine and pseudoephedrine as a decongestant is prepared according to the following procedure:

Stage I 30 kg pseudoephedrine sulfate, 60 kg hydroxypropyl methylcellulose (Methocel®K100M), 7.25 kg lactose monohydrate NF (spray dried) and 0.50 kg Cab-O-Sil (M5) are blended in a 10 cubic foot slant cone mixer with a speed of 17 rpm for 10 minutes. The mixture is passed through a Comil equipped with a #1143 screen and 0.175" spacer. The mixture is then further blended in a 10 cubic foot slant cone with a speed of 17 rpm for 30 minutes.

Stage II 0.75 kg of Mg Stearate and 1.5 kg of glyceryl monostearate (Eastman®600P) are passed through a 30 mesh screen and then blended with the mixture from STAGE I in a 10 cubic foot slant cone with a speed of 17 rpm for 30 minutes to form a tabletting blend.

Stage III

The tabletting blend from STAGE II is compressed into standard concave oval 0.3640 "x0.7280 shaped tablets each with a target weight of 800 mg, and containing 240 mg of pseudoephedrine sulfate. The tablets are formed using pre-compression and a manesty tablet press with a press speed of 30 rpm and a final target hardness value of 23 kp. The precompression force is 3 to 4 kp.

Stage IV

The compressed matrix core tablets from STAGE III are coated with an immediate release dose of loratadine by coating the compressed matrix tablet with an aqueous suspension comprising:

| | |
|---|---|
| 1. Loratadine, micronized | 1.16 kg |
| 2. Opadry ® Clear YS-1-7006 | 4.32 kg |
| 3. Talc, USP | 1.16 kg |
| 4. Sodium Lauryl Sulfate, NF | 2.32 kg |
| 5. Purified water, USP | 89.63 kg |

An excess of 3% of loratadine, Opadry Clear®, talc, and sodium lauryl sulfate may be added to compensate for loss in manufacturing. The immediate release layer is prepared by placing the Opadry Clear® and purified water into a 25 gallon container then adding the Sodium Lauryl Sulfate and talc and loratadine. Stirring of the talc suspension is continued. The suspension is then sprayed onto the matrix core tablets to form an external immediate release layer of loratadine under the following conditions:

| | | |
|---|---|---|
| Exhaust temperature: | 43 +/– 5° | C. |
| Atomization pressure: | 35 +/– 10 | psi |
| Fan air Pressure: | 35 +/– 10 | psi |
| Piston air pressure: | 40 +/– 10 | psi |
| Air volume: | 1500 +/– 300 | CFM |
| Pan Speed: | 4–8 | rpm |
| Spray Rate: | 250 +/– 100 | g/min |
| Nozzle distance: | 11 +/– 1" | |

Stage V

The immediate release coated tablets prepared in STAGE IV are then coated with a composition comprising a colorant and wax:

| | |
|---|---|
| Opadry White ® YS-1-7003 | 4.64 kg |
| Purified water | 46.40 kg |
| Candellila Wax Powder, FCC | 0.03 kg |

This color coating is applied by placing the immediate release coated compressed matrix tablets from STAGE V into a perforated pan coater. The suspension is sprayed onto the tablets to form a color layer under the following conditions:

| | | |
|---|---|---|
| Exhaust temperature: | 43 +/– 5° | C. |
| Atomization pressure: | 35 +/– 10 | psi |
| Fan pressure: | 35 +/– 10 | psi |
| Piston air pressure: | 40 +/– 10 | psi |
| Air volume: | 1500 +/– 300 | CFM |
| Pan Speed: | 4–8 | rpm |
| Spray Rate: | 250 +/– 100/min | |
| Nozzle distance: | 11 +/– 1" | |

Figure 2:
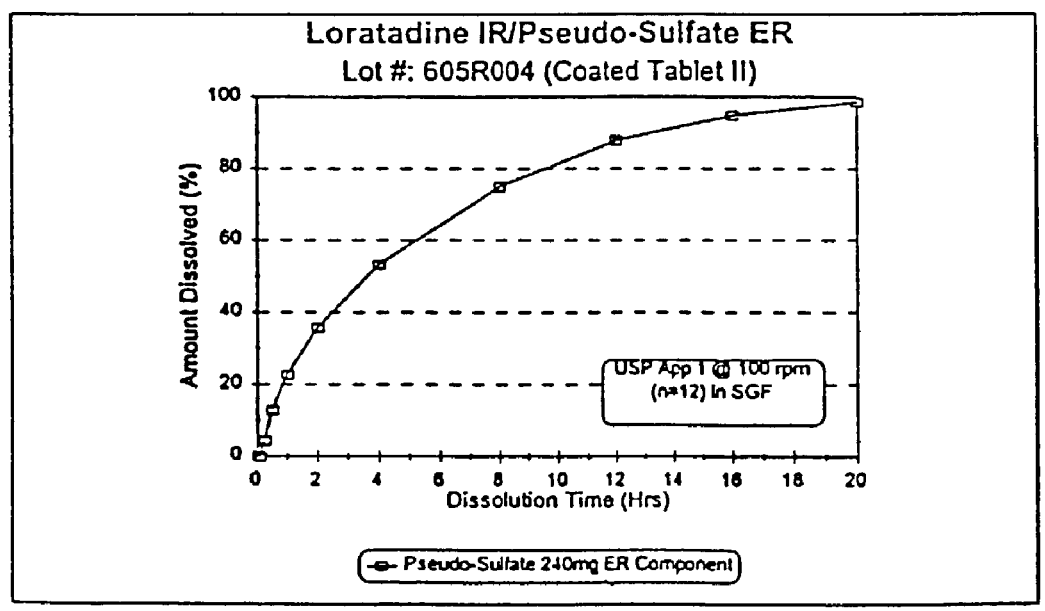
FIG. 2 is a graph which shows the in vitro dissolution rate of a decongestant from a tablet of a preferred embodiment of the present invention in SGF buffer.

The once daily antihistamine/ decongestant formulation prepared in this example was tested using a USP App. 1@ 100 rpm, 37° C. and 900 ml of simulated gastric fluid (SGF) buffer. The results of the dissolution testing are shown in FIGS. 1 and 2.

Figure 3:
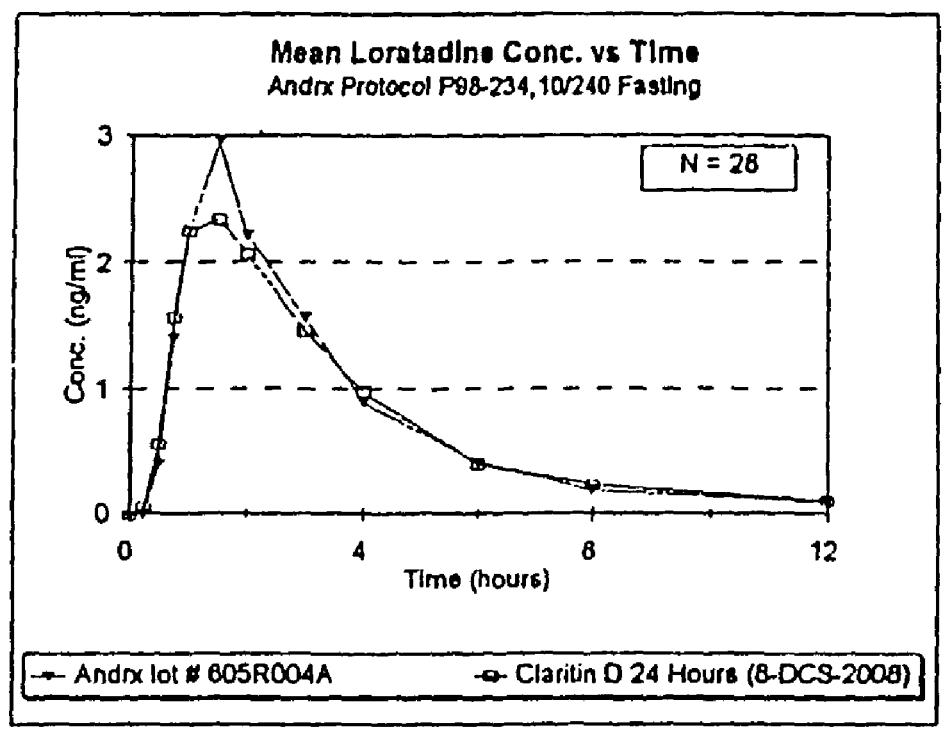
FIG. 3 is a graph which shows in vivo human blood concentration levels of loratadine from a tablet of a preferred embodiment of the invention after administration under fasting conditions.
Figure 4:
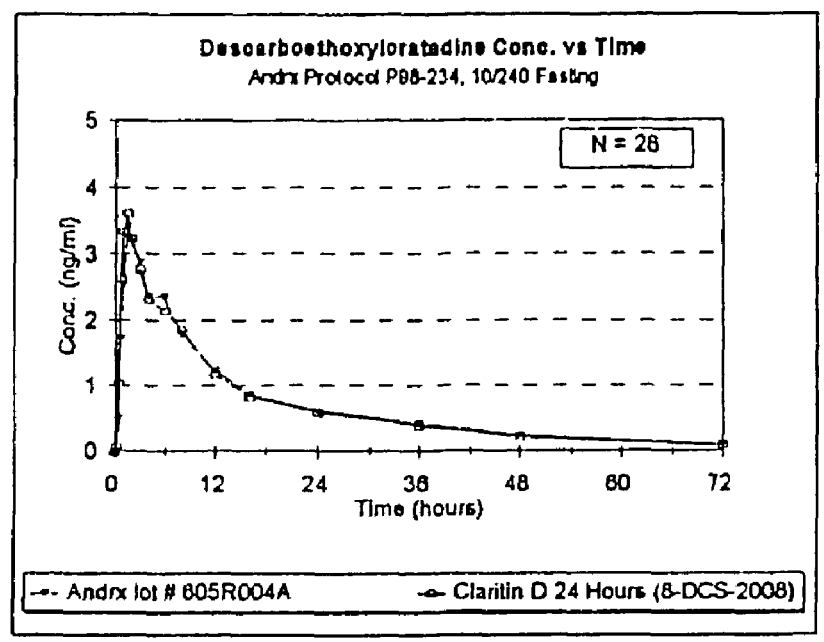
FIG. 4 is a graph which shows in vivo human blood concentration levels of descarboethoxyloratadine from a tablet of a preferred embodiment of the invention after administration under fasting conditions.
Figure 5:
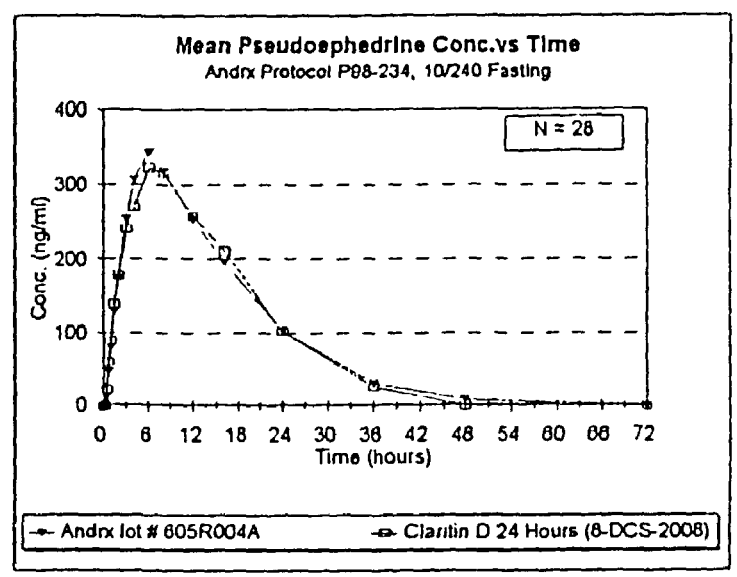
FIG. 5 is a graph which shows in vivo human blood concentration levels of pseudoephedrine from a tablet of a preferred embodiment of the invention after administration under fasting conditions.

The formulation of the preferred embodiment was used to conduct in vivo tests for blood levels of loratadine, pseudoephedrine and descarboethoxyloratadine as compared to CLARITIN® D24 and the results are shown in FIGS. 3, 4 and 5 respectively. The results show the bioequivalence of the preferred embodiment to CLARITIN® D24.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical formulation consisting essentially of:
   (A) a compressed matrix core consisting of:
      (i) 10 to 50 weight percent based on the total weight of the matrix core of a decongestant or pharmaceutically acceptable salt thereof;
      (ii) 50 to 90 weight percent based on the total weight of the matrix core of a hydrogel forming polymer "selected from the group consisting of hydroxypropyl methylcellulose, carboxymethylcellulose calcium, carboxymethylcellulose sodium, guar gum, hydroxyethyl cellulose, hydroxypropyl cellulose, methyl cellulose, acrylic acid crosslinked with polyalkenyl ethers or divinyl glycol, sodium alginate and polyethylene oxide";
      (iii) 0 to 20 weight percent based upon the total weight of the matrix core of a filler selected from lactose, starch, dextrose or sucrose;
      (iv) 0 to 5 weight percent based on the total weight of the matrix core of a glidant;

(v) 0 to 10 weight percent based on the total weight of the matrix core of one or more lubricants;
(B) an immediate release coating on said compressed matrix core which consists essentially of:
  (i) 0.01 to 10 weight percent based on the total weight of the formulation of an antihistamine
  (ii) 0 to 20 weight percent based upon the total weight of the formulation of a pharmaceutically acceptable binder which allows for immediate release of the antihistamine
  (iii) 0 to 10 weight percent based on the total weight of the formulation of a lubricant; and
  (iv) 0 to 10 weight percent based on the total weight of the formulation of an antiadherent; and
(C) optionally a polishing agent or color coating that coats the immediate release coating.

2. The formulation as defined in claim 1 wherein the hydrogel forming polymer is hydroxypropyl methylcellulose with an average molecular weight of 180,000 to 220,000.

3. The formulation as described in claim 1 wherein said polishing agent comprises candellila wax.

4. The formulation as described in claim 1 wherein:
(A) the compressed matrix core consists of:
  (i) 20 to 40 wt % based on the total weight of the matrix core of a decongestant or pharmaceutically acceptable salt thereof;
  (ii) 55 to 75 wt % based on the total weight of the matrix core of a hydrogel forming polymer;
  (iii) 5 to 15 wt % based upon the total weight of the matrix core of a filler selected from lactose, starch, dextrose or sucrose;
  (iv) 0.01 to 2 wt % based on the total weight of the matrix core of a glidant; and
  (v) 0.01 to 5 wt % based on the total weight of the matrix core of a lubricant;
(B) the immediate release coating on said compressed matrix core which consists essentially of:
  (i) 0.01 to 5 wt % based on the total weight of the formulation of a non-sedating antihistamine
  (ii) 0.01 to 10 wt % based upon the total weight of the formulation of a pharmaceutically acceptable binder forming material which allows for immediate release of the non-sedating antihistamine (iii) 0.1 to 5 wt % based on the total weight of the formulation of a lubricant; and
  (iv) 0.1 to 5 wt % based on the total weight of the formulation of an antiadherent.

5. A once a day, antihistamine and decongestant formulation consisting essentially of:
(A) a compressed matrix core consisting of:
  (i) 10 to 50 wt % based on the total weight of the matrix core of pseudoephedrine or a pharmaceutically acceptable salt thereof;
  (ii) 50 to 90 wt % based on the total weight of the matrix core of a single hydrogel forming polymer "selected from the group consisting of hydroxypropyl methylcellulose, carboxymethylcellulose calcium, carboxymethylcellulose sodium, guar gum, hydroxyethyl cellulose, hydroxypropyl cellulose, methyl cellulose, acrylic acid crosslinked with polyalkenyl ethers or divinyl glycol, sodium alginate and polyethylene oxide";
  (iii) 0 to 20 wt% based on the total weight of the matrix core of a filler selected from lactose, starch, dextrose or sucrose;
  (iv) 0 to 5 wt % based on the total weight of the matrix core of an antiadherent;
  (v) 0 to 10 wt % based on the total weight of the matrix core of a lubricant; and
(B) an immediate release coating on said compressed matrix core which consists essentially of;
  (i) 0.01 to 10 wt % based on the total weight of the formulation of loratadine;
  (ii) 0.1 to 20 wt % based on the total weight of the formulation of a pharmaceutically acceptable binder material which allows for immediate release of the loratadine;
  (iii) 0 to 10 wt % of lubricant; and
  (iv) 0 to 10 wt % of antiadherent; and
(C) optionally, a polishing agent or color coating that coats the immediate release coating.

6. The formulation described in claim 5 wherein:
(A) the compressed matrix core consists of:
  (i) 20 to 40 wt % based on the total weight of the matrix core of pseudoephedrine or a pharmaceutically acceptable salt thereof;
  (ii) 55 to 75 wt % based on the total weight of the matrix core of a hydrogel forming polymer;
  (iii) 5 to 15 wt % based on the total weight of the matrix core of a filler selected from lactose, starch, dextrose or sucrose;
  (iv) 0.01 to 2 wt % based on the total weight of the matrix core of an antiadherent;
  (v) 0.01 to 5 wt % based on the total weight of the matrix core of a lubricant; and
(B) the immediate release coating on said compressed matrix core which consists essentially of;
  (i) 0.1 to 5 wt % based on the total weight of the matrix core of loratadine;
  (ii) 0.1 to 10 wt % based on the total weight of the matrix core of a pharmaceutically acceptable binder which allows for immediate release of the loratadine;
  (iii) 0.1 to 5 wt % of lubricant; and
  (iv) 0.1 to 5 wt % of antiadherent.

7. The formulation as defined in claim 5 wherein the polishing agent consists essentially of candellila wax.

8. The formulation as defined in claim 5 wherein the hydrogel polymer is hydroxypropyl methylcellulose having average molecular weight of 180,000 to 220,000.

9. The composition of claim 5 which exhibits the following blood level concentration of loratadine when administered under fasting conditions:
  (a) from 1.5 to 3.0 ng/ml of the loratadine after 2.0 hours;
  (b) from 0.75 to 1.5 ng/ml of loratadine after 4.0 hours;
  (c) from 0.25 to 0.5 ng/ml of loratadine after 6.0 hours;
  (d) from 0.1 to 0.3 ng/ml of loratadine after 8.0 hours.

10. The composition of claim 5 which exhibits the following blood level concentration of descarboethoxyloratadine when administered under fasting conditions:
  (a) from 1.5 to 2.5 ng/ml of descarboethoxyloratadine after 6.0 hours;
  (b) from 0.75 to 1.5 ng/ml of descarboethoxyloratadine after 12.0 hours;
  (c) from 0.5 to 1.0 ng/ml of descarboethoxyloratadine after 24.0 hours.

11. The composition of claim 5 which exhibits the following blood level concentration of pseudoephedrine when administered under fasting conditions:
  (a) from 50 to 150 ng/ml of pseudoephedrine after 3 hours;
  (b) from 200 to 300 ng/ml of pseudoephedrine after 6.0 hours;

(c) from 200 to 250 ng/ml of pseudoephedrine after 12.0 hours;
(d) from 175 to 225 ng/ml of pseudoephedrine after 18.0 hours;
(e) from 75 to 125 ng/ml of pseudoephedrine after 24.0 hours.

12. The formulation as defined in claim 1 wherein the antihistamine is a non-sedating antihistamine.

13. The formulation as defined in claim 1 wherein the antihistamine is a piperidinoalkanol compound.

14. The formulation as defined in claim 1 wherein the antihistamine is loratatdine.

15. The formulation as defined in claim 1 wherein the decongestant is a pseudoephedrine salt selected from the group consisting of sulphate, sodium, calcium, or hydrochloride.

16. The formulation as defined in claim 1 wherein the hydrogel forming polymer is hydroxypropyl methylcelluose with an average molecular weight greater than 180,000.

17. The formulation as defined in claim 1 wherein said filler is lactose.

18. The formulation as defined in claim 1 wherein said glidant in the matrix core is colloidal silicon dioxide.

19. The formulation as defined in claim 1 wherein said lubricant in the matrix core is a mixture of magnesium stearate and glyceryl monostearate.

20. The formulation as defined in claim 1 wherein said binder in the immediate release coating comprises hydroxypropyl methylcellulose.

21. The formulation as defined in claim 1 wherein said lubricant in the immediate release coating is talc.

22. The formulation as defined in claim 1 wherein the antiadherent in the immediate release coating is sodium lauryl sulfate.

23. The formulation as defined in claim 1 which exhibits the following antihistamine dissolution profile when tested in 900 ml of simulated gastric fluid buffer, pH 1.2, using a USP Type I apparatus at 100 rpm, 37° C..
   a) from 40 to 80 wt % of the antihistamine is released after 0.25 hours;
   b) from 65 to 95 wt % of the antihistamine is released after 0.5 hour;
   c) not less than to 85 wt % of the antihistamine is released after 1.0 hour.

24. The formulation as defined in claim 1 which exhibits the following antihistamine dissolution profile when tested in 900 ml of simulated gastric fluid buffer, pH 1.2, using a USP Type I apparatus at 100 rpm, 37° C.
   a) not less than 50 wt % of antihistamine released after 0.25 hour;
   b) not less than 75 wt % of antihistamine released after 0.5 hour;
   c) not less than 90 wt % of antihistamine released after 1.0 hour.

25. The formulation as defined in claim 1 which exhibits the following decongestant dissolution profile when tested in 900 ml of simulated gastric fluid buffer, pH 1.2, using a USP Type I apparatus at 100 rpm, 37° C.
   (a) from 0 to 50 wt % of the decongestant is released after 1.0 hour;
   (b) from 10 to 60 wt % of the decongestant is released after 2.0 hours;
   (c) from 20 to 70 wt % of the decongestant is released after 4.0 hours;
   (d) from 30 to 85 wt % of the decongestant is released after 8.0 hours;
   (e) not less than 45 wt % of the decongestant is released after 12.0 hours;
   (f) not less than 60 wt % of the decongestant is released after 20.0 hours.

26. The formulation as defined in claim 1 which exhibits the following decongestant dissolution profile when tested in 900 ml of simulated gastric fluid buffer at pH 1.2 using a USP Type I apparatus at 100 rpm at 37° C.
   (a) from 10 to 40 wt % of the decongestant is released after 1.0 hours;
   (b) from 15 to 45 wt % of the decongestant is released after 2.0 hours;
   (c) from 25 to 60 wt % of the decongestant is released after 4.0 hours;
   (d) from 35 to 80 wt % of the decongestant is released after 8.0 hours;
   (e) not less than 50 wt % of the decongestant is released after 12.0 hours;
   (f) not less than 70 wt % of the decongestant is released after 20.0 hours.

* * * * *